US012622991B2

(12) United States Patent
Clarke

(10) Patent No.: US 12,622,991 B2
(45) Date of Patent: May 12, 2026

(54) SCENT WINDOW SNIFFER CARD

(71) Applicant: John Clarke, Cheshire, CT (US)

(72) Inventor: John Clarke, Cheshire, CT (US)

( * ) Notice: Subject to any disclaimer, the term of this patent is extended or adjusted under 35 U.S.C. 154(b) by 0 days.

(21) Appl. No.: 18/826,564

(22) Filed: Sep. 6, 2024

(65) Prior Publication Data

US 2025/0090711 A1 Mar. 20, 2025

Related U.S. Application Data

(60) Provisional application No. 63/538,832, filed on Sep. 17, 2023.

(51) Int. Cl.
| | |
|---|---|
| *A61L 9/12* | (2006.01) |
| *A45D 40/00* | (2006.01) |
| *A61K 8/02* | (2006.01) |
| *B32B 3/26* | (2006.01) |
| *B32B 27/08* | (2006.01) |
| *B32B 27/10* | (2006.01) |
| *B32B 27/32* | (2006.01) |
(Continued)

(52) U.S. Cl.
CPC ............ *A61L 9/12* (2013.01); *A45D 40/0087* (2013.01); *A61K 8/02* (2013.01); *B32B 3/266* (2013.01); *B32B 27/08* (2013.01); *B32B 27/10* (2013.01); *B32B 27/32* (2013.01); *B32B 37/10* (2013.01); *B32B 37/12* (2013.01); *B32B 38/0004* (2013.01); *B32B 38/145* (2013.01); *B65D 75/26* (2013.01); *C08J 5/127* (2013.01); *B32B 2317/12* (2013.01); *B32B 2323/04* (2013.01); *C08J 2323/04* (2013.01); *C08J 2423/00* (2013.01); *C08J 2433/04* (2013.01)

(58) Field of Classification Search
CPC .... A61Q 13/00; A45D 40/0087; A45D 37/00; A45D 40/24; B32B 3/266; B32B 27/08; B32B 27/10; B32B 27/32; B32B 38/0004; B32B 38/145; B32B 2307/7248; B32B 2307/7265; B32B 2317/12; B32B 2323/04; B32B 2307/748; A61K 8/02; B65D 2203/12; B65D 85/72; B65D 83/00; B65D 75/26; A61L 9/12; C08J 5/127
See application file for complete search history.

(56) References Cited

U.S. PATENT DOCUMENTS 6,358,577 B1 * 3/2002 Bowen .................... B32B 27/32
239/57
2015/0283029 A1 * 10/2015 Riis ......................... B32B 15/20
206/438
(Continued)

FOREIGN PATENT DOCUMENTS

| WO | WO-9109731 A1 * | 7/1991 | ............. B32B 27/06 |
|---|---|---|---|
| WO | WO-9405182 A1 * | 3/1994 | ......... A45D 40/0087 |
| WO | WO-2005007518 A2 * | 1/2005 | ......... B32B 38/0008 |

OTHER PUBLICATIONS

Translation of WO 94/05182 A1 (Year: 2025).*

*Primary Examiner* — Scott R. Walshon

(57) ABSTRACT

A scent and freshener device and a method of manufacturing the device comprising a layered stack. The scent composition is encapsulated thus preventing leakage and the scent remains pure and uncompromised. A scent sniff card may hold one fragrance or multiple encapsulated fragrances. The scent sniff card is streamlined and uses minimal parts thus reducing manufacturing costs and landfill waste.

12 Claims, 4 Drawing Sheets

(51) Int. Cl.

| | | |
|---|---|---|
| *B32B 37/10* | (2006.01) | |
| *B32B 37/12* | (2006.01) | |
| *B32B 38/00* | (2006.01) | |
| *B65D 75/26* | (2006.01) | |
| *C08J 5/12* | (2006.01) | |

(56) References Cited

U.S. PATENT DOCUMENTS

| 2016/0186309 | A1* | 6/2016 | Henderson | B32B 3/26 |
| | | | | 427/458 |
| 2017/0000102 | A1* | 1/2017 | Parrinello | C08J 7/043 |
| 2017/0239915 | A1* | 8/2017 | Tracy | B32B 7/12 |
| 2018/0099064 | A1* | 4/2018 | Burns | A61L 9/12 |
| 2018/0161470 | A1* | 6/2018 | Zobele | A01M 29/12 |
| 2018/0170642 | A1* | 6/2018 | Dugonjic | B65D 77/2056 |
| 2021/0228759 | A1* | 7/2021 | Zobele | A61L 9/12 |

* cited by examiner

SCENT WINDOW SNIFFER CARD

CROSS REFERENCE TO RELATED APPLICATIONS

This application is being filed as a non provisional patent application, claiming benefit to provisional patent application 63/538,832, filed Sep. 17, 2023.

TECHNICAL FIELD

The present invention relates to a scent window sniffer card that provides a prospective consumer the opportunity to smell a fragrance of a product.

BACKGROUND OF THE INVENTION

It is known in the scent-fragrance art to provide small doses of scent samples to potential and existing customers to provide a sample of the scent of a product to assist their purchasing decision. There are different scent devices available that emit a fragrance that can be used to freshen up confined areas as cars, purses, gym bags, attaché cases, luggage, etc. Scent samplers are also used by package good companies, soap, deodorant, cleaner, perfume and any other companies wanting to introduce and distribute new fragrance scents for their products to prospective customers at point of sale, event parties, concerts, ballgames, magazine ads, and catalogs. Current scent sampling techniques include, scratch and sniff stickers, whereby the consumer scratches the surface of the printed paper to release the scent encapsulation mechanisms and experiences the scent; another technique known in the art is the "Snap & burst" paper, whereby the consumer breaks open the flap of the paper to break open the encapsulation to smell the scent; another type of scent sampler is the squeezable puffer, this device emits a mist of the fragrance when pressure is applied; another type of scent sampler is the overwrapped blotter paper with an injected scent oil. In this type of sampler, the oil is applied directly to an absorption blotter card paper. The oil and paper are overwrapped in a barrier film to prevent fragrance oil from immediately evaporating and preventing the corrosive oil meeting another surface. The blotter paper does not have a coating, so the printed reproduction of the paper is inferior and does not meet the four colors commercially printing standards for quality advertising magazine reproduction.

SUMMARY OF THE INVENTION

The present invention is drawn to an innovative scent and freshener device that does not have the shortcomings of known scent devices in the prior art. The present invention does not rely on known scent encapsulation techniques that result in a product with a contaminated scent profile. The prior art encapsulation processes adulterate the fragrance resulting in an inaccurate and distorted rendition of the intended scent. The contamination of the fragrance is due to the prior art encapsulation process that relies on high heat, inclusion of additional additives, and adhesives to create the encapsulation shell for holding the fragrance. The prior art scent substances are also contaminated if the sniff tester device requires scratching the area to release the scent molecules as mechanical activation of the fragrance area releases both the intended scent and the chemical molecules in the paper thereby creating an inaccurate scent profile of the sample. Similarly, rubbing the paper to activate and release the scent creates an adulterated scent profile as the scratching or rubbing the fragrance saturated area of the sample contaminates the sample with any products on the consumers hands, nails, or skin.

Also known in the art are the squeezable puffers of U.S. Pat. No. 8,777,127. This puffer device comprises a paper shell that houses a polyurethane foam. The fragrance oil is injected into the foam. When the shell and foam are squeezed the fragrance scent is released. However, the fragrance oil is contaminated by absorbing the residual odor molecules of the foam, thus resulting in a distorted scent profile. Additional adulteration of the fragrance oil occurs when it is exposed to ambient air, thus the foam and fragrance oil housed in the interior of the shell absorb surrounding scents, further tainting the intended fragrance. Another shortcoming of this type of device is that the oil injected into the foam is limited by the amount to help prevent leakage onto the paper shell which results in a weakened and shorter life scent release. The oil can also stain the paper and cause the advertising printing inks to run and be compromised on the paper impeding production. Another problem with this squeezable device is that the fragrance molecules that are forced out as a puff can get into the consumer eyes or nose causing irritation, skin rashes, allergic reactions, and other unwanted effects.

The overwrapped blotter paper with injected scent device is another device known in the art it requires the consumer to cut, with a cutting instrument, as a scissor, the seal of the barrier overwrap film and slowly slip the paper through the opening of the film on a gradual timetable. Several problems are posed by this device, namely it is not a convenient and easy-to-use scent sniffing device, which may deter the consumer from smelling the sample and bypass the purchase of the product. Additionally, the clumsy stepped release of the film is required because if the scent release film is lifted too fast the fragrance oil evaporates very quickly resulting in a short product life. Another problem faced in the art is the corrosive nature of the fragrance oil. The oil corrodes plastic, laminates, and wood surfaces. Another concern is the contact with a consumer skin and bodily parts; warnings by the manufacturer are placed on these devices warning the consumer about the risk of corrosion on surfaces and irritation to the skin, throat, eyes, and nose.

The present invention is based on a scent window sniff card sampler device and its manufacturing process. The process to make the scent sniff card is simplified from the prior art and results in a scent sniff card using minimal components which results in a compact and effective, easy to use, unadulterated fragrance scent experience. Another benefit of the scent window sniffer card of the instant invention is the capability to provide multiple scent sampling in one card, yet another benefit is the reduction of parts to manufacture the scent window sniff card thus reducing landfill waste.

The scent sniff card of the instant invention is manufactured by using the original, pure un-encapsulated fragrance composition such as an oil for the consumer to experience. The process does not print the fragrance oil encapsulation on paper thus eliminating malodorous scents and inks. The process does not require mechanical scratching, rubbing, or bursting the paper by the holder to release the scent. The result is a streamlined fragrance tester or freshener card that releases a pure, uncontaminated scent.

An embodiment of the invention is the process of making the scent window sniff card sampler, which results in a streamlined card with encapsulated fragrance areas. Another embodiment of the invention is a scent sniff card comprising a plurality of fragrance release areas, wherein each area contains the same fragrance composition such as an oil. Another embodiment of the invention is a scent sniff card comprising a plurality of scent release areas, wherein each area contains a unique fragrance oil, resulting in a single scent card having multiple scents in a single card.

BRIEF DESCRIPTION OF THE DRAWINGS

The present disclosure will be better understood by those skilled in the pertinent art by referencing the accompanying drawings.

DETAILED DESCRIPTION OF THE INVENTION

Figure 1:
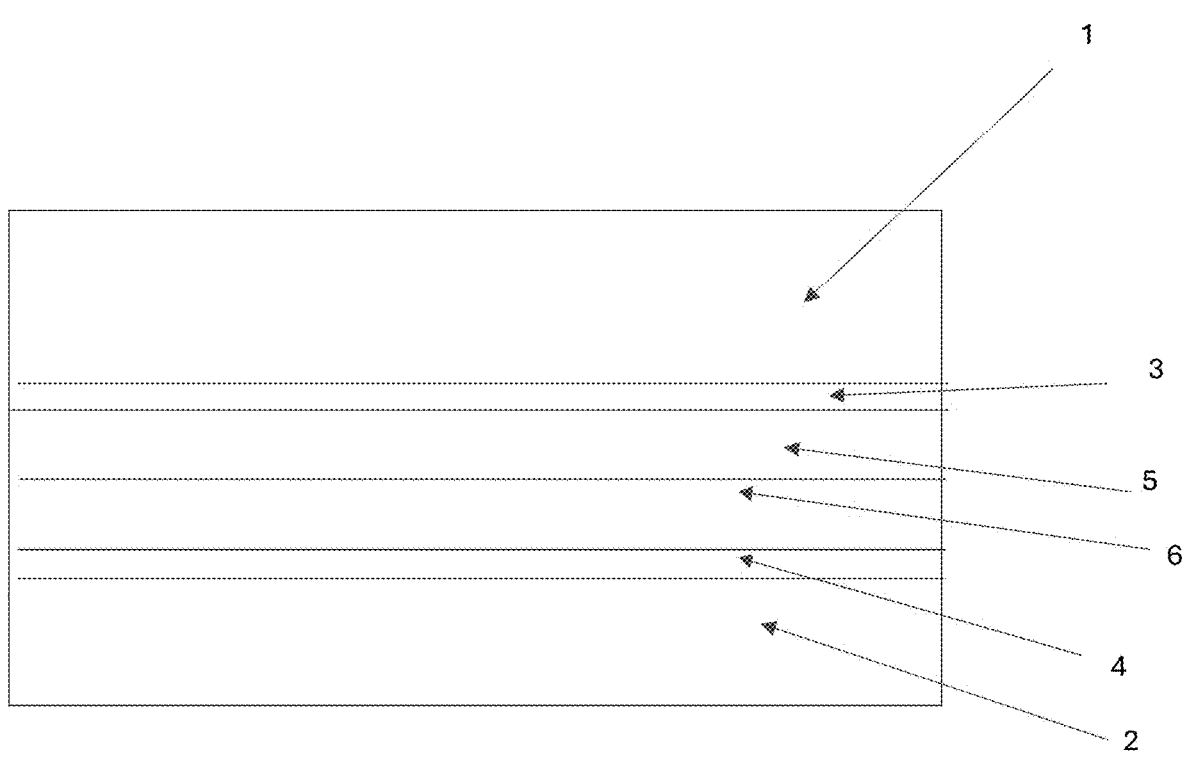
FIG. 1 is a cross section of the scent window sniff card layers.
Figure 2A:
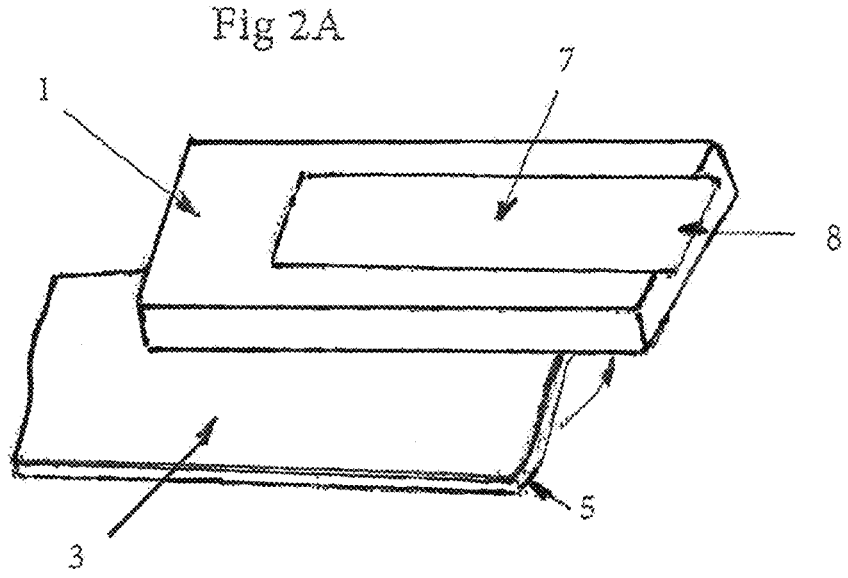
FIG. 2A is a top view of one side of a first laminate stack of the scent sniff card.
Figure 2B:
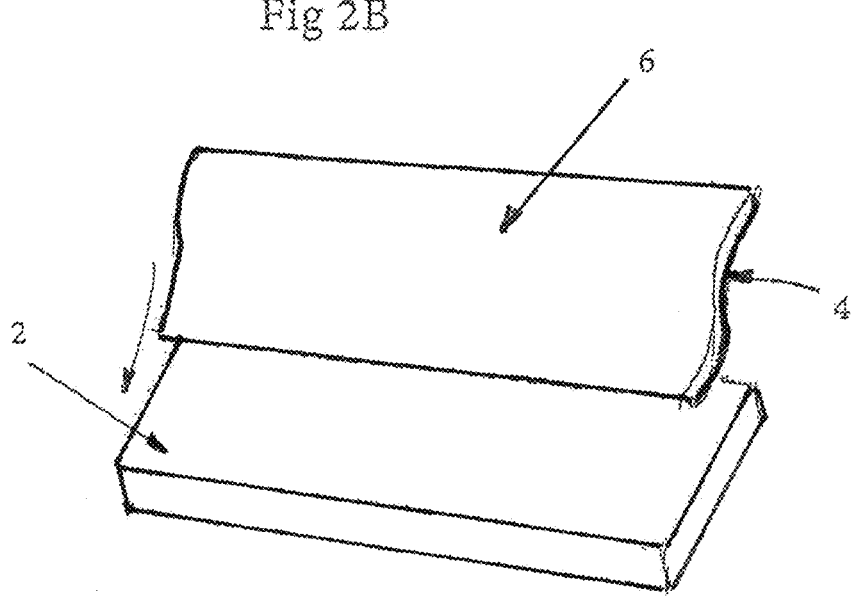
FIG. 2B is a bottom view of one side of a second laminate stack of the scent sniff card.

The invention is best described by referring to the figures. FIG. 1 is a cross section of a scent card and its layers. The scent card comprises a first and second substrate 1 and 2 each substrate having an adhesive layer 3 and 4 on the underside. The substrates 1 and 2 may be any substrate material that is conducive to lamination, the preferred substrate comprises card stock, preferably an eight-point quality coated paper tag stock. The adhesive layers 3 and 4 comprise a water-based adhesive. A preferred water-based adhesive comprises a dried-film stabilized vinyl acrylic copolymer emulsion. An impermeable barrier layer 5 affixed to the first adhesive layer 3 and second impermeable barrier layer 6 is affixed to the second adhesive layer 4. The impermeable barrier layers 5 and 6 are adjacent thereto. The impermeable layer is preferably low-density polyethylene, most preferably 0.001-0.003 mil low density polyethylene. FIGS. 2A and 2B each show half of a rectangular shaped scent sniff card where 2A shows substrate 1 having a perforated cut-out window aperture 7 which prevents scent transfer until lifted by user. A pull tab 8 is incorporated to facilitate ease of lifting cut-out window aperture. The aperture cut-out window is held on with notches or perforations. An application of scent oil is applied between impermeable barriers 5 and 6 in stack of FIGS. 2A and 2B. Impermeable barriers 5 and 6 of stack 2A and 2B are joined together to comprise a scent sample card. The bonding of the laminating polymers affixed to the substrate with the application of scent oil between creates a sealed area which allows the molecular transfer of scent aroma to escape while preventing wet oil transfer. The preferred method to join the impermeable layers 5 and 6 to ensure a secure bond of impermeable layers is through heat sealing.

Figure 3:
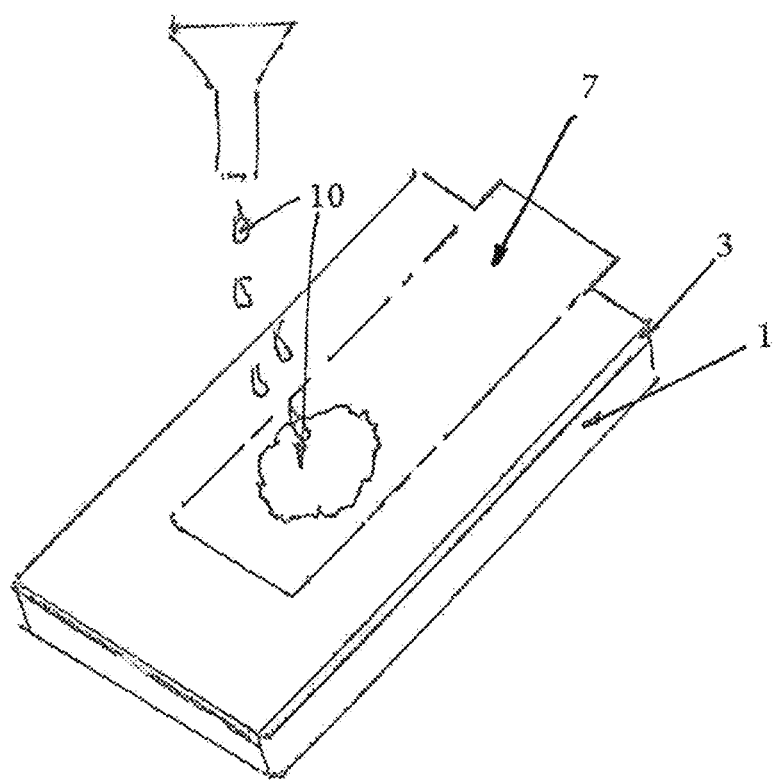
FIG. 3 is a top view of the laminated paper board piece of the scent sniff card with a scent oil placement on the polymeric film.
Figure 4:
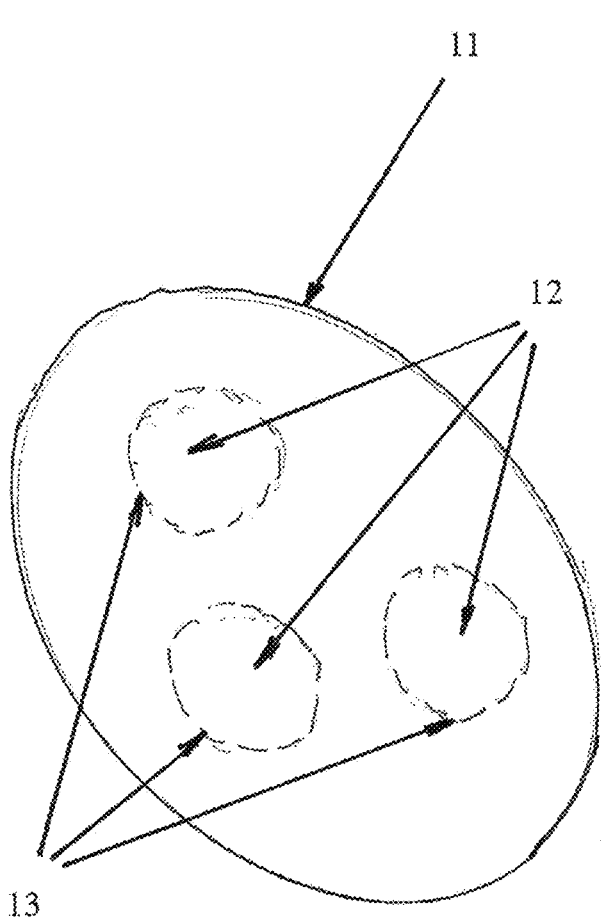
FIG. 4 is a view of the front laminated board comprising multiple apertures.

Another embodiment of the invention demonstrated in FIG. 3, comprises a scent card stack shown impermeable layer 3 facing up wherein the layered substrate 1 containing a perforated aperture 7 is below. Scent oil application 10 is placed on impermeable layer 3 above perforated aperture. The invention is adaptable to having a single aperture on one side as seen in FIG. 3, which is conducive to a single fragrance scent card. Alternatively, the scent card may comprise multiple apertures on either side of the scent window scent card as seen in FIG. 4, wherein the fragrance oil or composition encapsulated on each side may be the same scent, or alternatively a different scent may be encapsulated in each of the apertures to give the consumer multiple scent samplings in only one scent window sniffer card. FIG. 4 demonstrates a scent card 11 having a circular shape, it is understood that any shape such as rectangular, square, oval, octagonal or any other shape is usable for the scent card. Similarly, the size of the card is adaptable to the intended manufacture. The size may be dependent on the number of apertures and fragrance profiles the scent card contains as a final product. Similarly, a plurality of apertures 12 may be cut on only one side of the substrate or alternatively a plurality of apertures may be cut on both substrates dependent on the number of fragrance profiles included in the final product. Each aperture having the window cutouts 13 held in place with perforations or notches and although not shown the final scent sniff card having the multiple apertures comprises the same elements as those shown in FIG. 1 and the scent sniff card of FIG. 2A and FIG. 2B.

Multiple fragrance profiles can be economically manufactured on one scent card, giving the consumer the ability to smell various fragrances of a product line or multiple products and resulting in an efficient, economical, and streamlined scent sampler. It is also understood that the substrates 1 and 2 may contain custom printing reflecting the company's logos, marketing strategy, product profile and fragrance identification. The custom printing may be the same on both substrates 1 and 2, or each substrate may reflect a different product and fragrance profile. The scent compositions may be an oil or other known scent compositions in the art. The concentration injected in each aperture is dependent on the size of the aperture, the viscosity of the oil and other properties of the scent composition.

Another embodiment of the invention is the process for making the scent window sampler card. The process comprises feeding a substrate such as an 8 point stock card paper through an in-line press; custom printing the substrate, cutting an aperture in the substrate with a rotary steel die, said aperture is kiss cut and the cut-out window is held with notches or perforations; applying a self-wound polypropylene over the printed surface of the paper stock. A hinge and tab for the consumer to lift cut-out window and activate the scent or scents of the final product; turning over the laminated substrate, applying an adhesive on the un-laminated side of the substrate such as dried film stabilized vinyl acrylic copolymer emulsion; applying an impermeable layer, preferably a light weight 0.001 to 0.003 mil polyethylene polymer film thus making a laminated stack piece; die-cutting the laminated sheet into single laminated stack pieces, turning over the laminated substrates such that the printed side faces down and the impermeable layer film faces up; injecting a predetermined amount of a scent composition preferably an oil, on the impermeable barrier polymer film; aligning the impermeable layer of one laminated stack piece on top of the impermeable layer of a second laminated stack piece so that the impermeable barrier polymer films are in contact with each other; pressing the two-piece substrate stack; and heat sealing the two substrates only on the outside of the scent apertures thereby encapsulating the scent composition and bonding the stack into a single laminated scent card. A method of making a scent sniff card comprising: feeding a substrate through an in-line press; custom printing a first side of the substrate; cutting an aperture in the substrate with a rotary steel die, said aperture is kiss cut and a cut-out window is held with notches or perforations; applying an adhesive coating layer on the substrate underside; applying an impermeable barrier layer over the adhesive coating layer, creating a laminated stack; die-cutting the laminated stack into single laminated stack pieces; positioning the laminated stack pieces for injecting an amount of a scent composition on the impermeable barrier layer opposite kiss cut aperture window; aligning the impermeable layer of the inside of the laminated stack piece on top of the impermeable layer of a second laminated stack piece; pressing the two-piece substrate stack; and heat sealing the two-piece laminated stack only on the outside of the scent apertures thereby encapsulating the scent composition and bonding the stack into a single laminated scent card. Additionally, may comprise kiss-cutting a plurality of apertures on the substrate and injecting at least one scent composition in the apertures. Additionally, wherein the substrate may comprise card stock. Additionally, wherein the impermeable barrier layer comprises low density polyethylene. Additionally, wherein the substrate may comprise card stock and the impermeable barrier layer comprises low density polyethylene and the adhesive layer comprises a water based stabilized vinyl acrylic copolymer.

While the disclosure has been described with reference to several embodiments, it will be understood by those skilled in the art that various changes may be made, and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the embodiments disclosed as the best mode contemplated for carrying out this disclosure, but that the disclosure will include all embodiments falling within the scope of the appended claims.

What is claimed is:

1. A fragrance scent sniff card consisting essentially of:
a first substrate, a first adhesive on the inside of the first substrate; a first impermeable barrier polymer on the inside of the first substrate; the first impermeable to oil-permeable to vapor barrier polymer adhered to the first adhesive; a second adhesive on the inside of a second substrate, a second impermeable to oil-permeable to vapor barrier polymer adhered to the second adhesive, wherein the first and second impermeable to oil-permeable to vapor barrier polymers are adjacent thereto and a fragrance scent oil composition encapsulated between first and second impermeable to oil-permeable to vapor barriers; wherein the impermeable to oil-permeable to vapor barrier layers allow the molecular transfer of the fragrance scent oil to escape and prevents the outward passage of the fragrance scent oil.

2. The scent sniff card of claim 1 wherein the first and second impermeable barrier polymers comprise low density polyethylene.

3. The scent sniff card of claim 1 further comprising at least one perforated cut aperture and a pull and lift tab cut on the first substrate.

4. The scent sniff card of claim 3 wherein the first and second substrates are printed.

5. The scent sniff card of claim 3 further comprising a plurality of perforated cut apertures on first and second substrates; each aperture comprises the same or different fragrance scent oil compositions.

6. The scent sniff card of claim 1 wherein the adhesive layers comprise a water-based adhesive.

7. The scent sniff card of claim 1 wherein the first and second substrates are printed.

8. A method of making the scent sniff card of claim 1 comprising:
feeding a substrate through an in-line press;
custom printing a first side of the substrate;
cutting an aperture in the substrate with a rotary steel die, said aperture is kiss cut and a cut-out window is held with notches or perforations;
applying an adhesive coating layer on the substrate underside;
applying an impermeable barrier layer over the adhesive coating layer, creating a laminated stack;
die-cutting the laminated stack into single laminated stack pieces;
positioning the laminated stack pieces for injecting an amount of a scent composition on the impermeable barrier layer opposite kiss cut aperture window;
aligning the impermeable layer of the inside of the laminated stack piece on top of the impermeable layer of a second laminated stack piece;
pressing the two-piece substrate stack; and heat sealing the two-piece laminated stack only on the outside of the scent apertures thereby encapsulating the scent composition and bonding the stack into a single laminated scent card.

9. The method of making a scent sniff card according to claim 8, further comprising kiss-cutting a plurality of apertures on the substrate and injecting at least one scent composition in the apertures.

10. The method of making a scent sniff card according to 8, wherein the substrate comprises card stock.

11. The method of making a scent sniff card according to 8, wherein the impermeable barrier layer comprises low density polyethylene.

12. The method of making a scent sniff card according to claim 8 wherein the substrate comprises card stock and the impermeable barrier layer comprises low density polyethylene and the adhesive layer comprises a water based stabilized vinyl acrylic copolymer.

* * * * *